United States Patent [19]
Potter

[11] Patent Number: 5,589,195
[45] Date of Patent: Dec. 31, 1996

[54] FILM-FORMING PROTEINACEOUS EMULSION

[75] Inventor: Richard C. Potter, Seeley Lake, Mont.

[73] Assignee: Nurture, Inc., Missoula, Mont.

[21] Appl. No.: 215,286

[22] Filed: Mar. 21, 1994

Related U.S. Application Data

[63] Continuation of Ser. No. 505,126, Apr. 5, 1990.

[51] Int. Cl.$^6$ ............................. A61K 7/00; A61K 9/107
[52] U.S. Cl. ................. 424/499; 424/78.03; 424/401; 424/418; 424/420; 424/439; 427/372.2; 514/937; 514/951
[58] Field of Search ...................... 424/401, 420, 424/78.03, 418, 499; 427/372.2; 514/937, 951

[56] References Cited

U.S. PATENT DOCUMENTS

| | | | |
|---|---|---|---|
| 1,855,934 | 4/1932 | Banks et al. | 106/541.1 |
| 2,355,029 | 8/1944 | Musher | 252/1 |
| 2,436,818 | 3/1948 | Musher | 424/49 |
| 2,754,215 | 7/1956 | Evans et al. | 426/96 |
| 2,876,164 | 3/1959 | Wershaw | 514/772.5 |
| 3,318,536 | 5/1967 | Graumann | 241/6 |
| 3,394,119 | 7/1968 | Luce et al. | 530/334 |
| 3,676,357 | 7/1972 | Ciuti et al. | 502/402 |
| 3,714,063 | 1/1973 | Salomone | 252/312 |
| 3,755,560 | 8/1973 | Dickert et al. | 514/772.6 |
| 3,885,052 | 5/1975 | Starr | 426/250 |
| 4,014,995 | 3/1977 | Juliano et al. | 514/783 |
| 4,217,370 | 8/1980 | Rawlings et al. | 426/98 |
| 4,218,482 | 8/1980 | Cook et al. | 426/72 |
| 4,238,509 | 12/1980 | Evans et al. | 514/777 |
| 4,246,257 | 1/1981 | Elliott et al. | 424/78.03 |
| 4,341,799 | 7/1982 | Good | 514/784 |
| 4,435,429 | 3/1984 | Burrows et al. | 426/18 |
| 4,734,287 | 3/1988 | Singer et al. | 426/41 |
| 4,826,818 | 5/1989 | Mori et al. | 514/21 |
| 4,855,156 | 8/1989 | Singer et al. | 426/565 |
| 5,023,080 | 6/1991 | Gupta | 424/405 |
| 5,026,548 | 6/1991 | Evans et al. | 424/195.1 |

FOREIGN PATENT DOCUMENTS

| | | |
|---|---|---|
| 0146174A1 | 6/1985 | European Pat. Off. . |
| 2287214 | 5/1976 | France . |
| 2571253 | 4/1986 | France . |
| 56-015203 | 2/1981 | Japan . |
| 57-074384 | 5/1982 | Japan . |

OTHER PUBLICATIONS

John Coe & Angelo Juliano "A New Natural Ingredient for Cosmetic Formulators" D&CI; pp. 48–56 (Sep. 1973).

Primary Examiner—John C. Bleutge
Assistant Examiner—Robert H. Harrison
Attorney, Agent, or Firm—Knobbe, Martens, Olson & Bear

[57] ABSTRACT

A proteinaceous emulsion and method for making a proteinaceous emulsion comprising a lipophilic phase, an aqueous phase and a protein emulsifier; which is capable of forming a thin film and has the capability of carrying active ingredients contained in either or both the aqueous phase and the lipophilic phase of the emulsion.

12 Claims, 3 Drawing Sheets

EFFECT OF PROTEIN CONTENT ON EMULSION VISCOSITY

NOTE: CANNON-FENSKE VISCOMETER, SIZE 400;
AIR TEMP.=24.5°C; 10ml SAMPLE SIZE;
EACH POINT IS AVERAGE OF 3 REPLICATES

FILM-FORMING PROTEINACEOUS EMULSION

This application is a continuation of application Ser. No. 07/505,126, filed Apr. 5, 1990.

BACKGROUND OF THE INVENTION

Conventional oil-in-water or water-in-oil emulsions, particularly those used for topically applied cosmetics and pharmaceuticals and agricultural sprays, are prepared with considerable heating and high-shear mixing, and generally require a multiplicity of ingredients to ensure suitable emulsification.

Additionally, these formulations may contain a myriad of other ingredients in order to achieve a useful balance of emulsification, viscosity, and stability. Also, the production of satisfactory emulsions is energy intensive, entailing the use of high shear for mixing the phases and prolonged exposure to elevated temperatures.

Commonly known emulsions, particularly those comprising skin creams and lotions, are formulated with at least one and not atypically several emulsifiers which assist in the formation of the oil-in-water or water-in-oil emulsions. Typical emulsifiers comprise a variety of synthetic chemicals, including laureth-4, steareth-10 and PEG-5 lauramide. The use of such synthetic emulsifiers, particularly for topical skin applications, raises the specter of consumer safety concerns such as potential skin irritation and sensitization via exposure to synthetic or biologically non-compatible agents.

Certain animal proteins, usually hydrolyzed, are used in small concentrations as substantive coatings for skin and hair. These materials are solubilized, as opposed to having colloidal properties, and problems with viscosity, stickiness, and odor limit their concentration in a formulation and limit their service as useful emulsifiers. However, these materials are not recognized as having the ability to form useful emulsions for topical application of active ingredients. Moreover, because these animal proteins have been chemically hydrolyzed, they are not naturally occurring and carry some risk of skin irritation.

In addition, oils and/or oily substances are common constituents in topical skin applications, specifically cosmetic creams and lotions. These oils and/or oily substances are desirable additions to such topical applications in that they tend to form a thin, fluid film which retards the drying of the skin after evaporation of other volatile ingredients found in the cream or lotion. However, it is also desirable to reduce the greasy or oily feel of these creams and lotions on the skin. In order to achieve a non-oily skin feel, the resulting film should be either very thin or contain very little oil.

Thus, presently known lotion and cream formulations generally comprise oil-in-water emulsions and/or are preferably applied to the skin in a very thin film. In either case, the resultant film is not efficient as an occlusive film for preventing moisture loss from the skin and may still contain an undesirable amount of oil. Also, such films are easily rubbed off, thus allowing dehydration of the skin and a resultant uneven application of active ingredients contained therein.

Other attempts documented in the prior art to improve the film characteristics of such topical skin applications include the addition of synthetic film-forming polymers to the skin lotion or cream. In practice, the concentration of the polymer in the formulation is usually quite low, on the order of only a few percent, in order to avoid the undesirable aesthetics of a polymeric coating on the skin. Additionally, higher polymer concentrations generally result in formulation viscosities which are too high for practical use.

However, the use of low concentrations of polymer also limits the amount of oil which can be bound into the film, thereby limiting the effectiveness of the film as a moisture entrapper over the skin and/or carrier of active ingredients. Moreover, the addition of synthetic polymers to a topical lotion is less desirable from a consumer standpoint in terms of safety concerns.

The present invention overcomes all of the above objections by utilizing natural proteinaceous materials which not only act as emulsifiers to emulsify a lipophilic phase with an aqueous phase, but also produce resultant thin films. These films may preferably have non-oily, dry, flexible, occlusive, invisible and/or substantive properties, and can form films on surfaces such as skin, hair, and other surfaces such as plant leaves and other vegetation. It has been found that virtually any lipophilic constituent, including oils or oily substances, can be readily emulsified with these proteinaceous materials. These phases include emollients, oil-based vitamins, defoliants, essential oils, flavorants, sunscreen agents, insect repellents, pharmaceuticals and the like along with other active ingredients which are soluble or can be carried in the lipophilic phase. Additionally or alternatively, similar active ingredients can comprise the aqueous phase of the emulsion of the present invention.

Another surprising aspect of this invention is that the emulsions can be formed spontaneously at room temperature and with minimal agitation. Also, the proteinaceous emulsifiers of the invention are totally natural and are extremely safe to use.

The emulsions of the present invention are typically off-white, smooth, creamy, and may preferably dry quickly when applied as a thin film to a surface. Also, since the proteinaceous materials of the invention serve in a multiple capacity as emulsifiers, co-emulsifiers, thickeners, whiteners and film-formers, a minimal number of ingredients is required to build a useful formulation.

SUMMARY OF THE INVENTION

According to the present invention, a proteinaceous emulsion for delivering an active ingredient is provided, comprising an emulsifier consisting essentially of a proteinaceous material; an aqueous phase; a lipophilic phase; and an active ingredient. The active ingredient may comprise one or more compatible active ingredients, and may reside in the aqueous phase, the lipophilic phase or both. The active ingredient may preferably comprise an active ingredient suitable for topical applications, and may preferably be a pharmaceutical, pesticide or cosmetic agent.

In another aspect of the present invention, a method for making an emulsion is provided, comprising the steps of providing an emulsifier consisting essentially of a proteinaceous material; providing a lipophilic phase; providing an aqueous phase; and combining the emulsifier, lipophilic phase and aqueous phase such that an emulsion is formed. The method may further comprise the step of providing one or more active ingredients, the active ingredient being soluble in either the lipophilic phase or aqueous phase of the emulsion. The method may further comprise the step of permitting the aqueous phase to evaporate, thus forming a film containing the proteinaceous material and any active ingredient.

In yet another aspect of the present invention, a method is provided for sequestering the lipophilic phase of an emulsion which comprises an aqueous phase and a lipophilic phase comprising the steps of: providing an emulsifier consisting essentially of a proteinaceous material; providing an aqueous phase; providing a lipophilic phase; combining the emulsifier, aqueous and lipophilic phases; and forming an emulsion wherein the protein particulate acts as an emulsifier for the lipophilic phase and the aqueous phase. The aqueous phase and/or the lipophilic phase may have contained therein or comprise an active ingredient, the active ingredient preferably comprising a pharmaceutical agent. Furthermore, the method may comprise the further step of sequestering the lipophilic phase to a substantial extent within the protein particulate of the present invention.

Further features and advantages of the present invention will become apparent from the Detailed Description of the Preferred Embodiments which follows, taken together with the claims and appended Figures.

DETAILED DESCRIPTION OF PREFERRED EMBODIMENTS

Advantageously, the present invention provides the emulsion formulator a means to greatly expand the range and kind of active agents as well as the proportions thereof in a variety of emulsions. The effect of the proteinaceous material is to permit such formulations to be prepared without exogenous emulsifiers.

The benefits and advantages of this invention may be found with a wide variety of emulsions, particularly formulations designed for applications as a uniform film; most particularly, for pharmaceutic and cosmetic application to the skin. For instance, the prevention or relief of dryness of the skin with emollient or hand lotions is an important benefit. Dryness or "chapping" of the skin results when there is insufficient hydration from lower epidermal areas, or an excessive loss of water from exposure of the skin to low humidities, or both. Heavy or continuous use of soaps, etc., contribute to a dry skin condition by removal of the protective lipid layer which provides "slip" and flexibility, as well as retards the transpiration of moisture.

Lotions containing emollients are used to prevent or care for a dry skin condition. However, emollients are oily or greasy materials, and their application to the skin leaves a greasy or oily feel, which of course is more pronounced the larger the proportion or amount of the emollient used. The formulations of this invention have the further desirable property of being readily removable by washing with soap and water. By "readily removable," it is meant that after application, the resultant dried thin film may be substantially removed by the ordinary day-to-day cleansing process of lathering soap and washing or showering. This invention permits the application of lotions which have the aforementioned beneficial effects, without the normally attendant oily or greasy effect after applying and drying conventional lotion.

This effect of the protein particulate on the dry characteristics of the lotion was quite unexpected in the absence of any polymeric or other additions to the formulation and also in view of the relatively high lipophilic (oily) phase concentration achieved in the emulsion of the present invention. Hand lotions containing a variety of medicants, in addition to emollients, may also be formulated according to this invention. Other skin care products may be prepared which replace part or all of the emollient with sunscreen agents, analgesic agents, insect repellents, pharmaceuticals and the like. Many other useful lotions and lotion additives will be apparent to the formulator of such pharmaceutic products.

To form the emulsion of the present invention, one need only choose an appropriate proteinaceous material to serve as the emulsifier, and then admix an appropriate amount of the proteinaceous material with a lipophilic phase and an aqueous phase to form the resultant emulsion. Either or both phases may preferably have solubilized therein or inherently comprise one or more of a variety of active ingredients which may be advantageously incorporated into the emulsion. Applicable emulsion composition ranges include the following:

Proteinaceous material: from about 6 to about 60% weight, wherein the protein content of the proteinaceous material can vary from between about 1 to about 100% weight, dry basis.

Lipophilic phase: from about 3 to about 50% weight

Aqueous phase: from about 30 to about 80% weight

The emulsion can also be formed by heating the lipophilic phase and/or aqueous phase (typically involving temperatures from 50° C. to 90° C.). Frequently, this will increase the viscosity of the emulsions of the present invention.

Active Ingredients

The particular active ingredient to be used can vary widely, including active ingredients which have applications as cosmetics, pharmaceuticals, foods and pesticides. Volatiles which are suitable for use as active ingredients include alcohol and various fragrance compounds. Ingredients suitable as active ingredients include DEET, para amino benzoic acid (PABA) or its derivatives, PARSOL (a trademark of Bernel Chemical Company), or other active sunscreen ingredients, as well as moisturizing ingredients such as urea and mineral oil.

Numerous dermatologically active materials are also suitable as active ingredients in the present invention, including benzoyl peroxide, salicylic acid, resorcinol and retinoic acid for ache, and a variety of deodorants. Additional pharmaceutically active ingredients can include antibiotics, fungicides, astringents, anti-inflammatory agents and antipyretics. Insecticides such as pyrethrum can be used in the emulsion of the present invention, as well as numerous agriculturally related compositions such as herbicides, fungicides, fertilizers and insecticides. The foregoing are only illustrative of a few of the many ingredients that can be utilized as active ingredients.

The application of the emulsion technology to food flavorings and essential oils is of considerable interest. Clearly, such materials can be used either alone, or in combination, as the lipophilic phase (or as a portion of the lipophilic phase) of the emulsion. For instance, d-limonene (a citrus-type essential oil) can serve as both the active ingredient and the lipophilic phase of the emulsion of the present invention.

Moreover, fresh flavors which have a significant water content (such as freshly squeezed citrus juice or freshly pressed onion juice) could be introduced into the emulsion via the aqueous phase. Combinations of such ingredients (aqueous phase) with essential oils (lipophilic phase) could be prepared as a single emulsion.

Emulsions of this type could be sprayed onto the surface of various dry food preparations during the manufacturing process, such as dried soup mixes, cake mixes, frozen pizza, and potato chips. The emulsion would be allowed to dry, hence forming an outer flavor-containing film; such a film would also be useful in helping to seal in moisture and freshness. Alternatively, the emulsion could be coated onto the surface of frozen food preparations and quick-frozen prior to drying of the emulsion; during cooking, the flavor would slowly release from the film and combine with the product. This would be particularly beneficial where fragile or unstable flavors are desired. In certain cases, the emulsion might be slurried with a food formulation and the mixture spray-dried to yield a flavored film on the resultant particles. In other cases, the emulsion could be sprayed on the outside surface of the package to prompt the consumer organoleptically as to the contents of the package.

Alternatively, the emulsion may be formed such that the flavorants or extracts may be entrapped to a substantial extent within the proteinaceous material so that their release is relatively reduced. This mode of emulsion formation has particular importance in instances where the extract or flavorant is to remain upon a food surface which is to be later consumed. During consumption, mastication by the consumer breaks up the structure of the proteinaceous material and releases the flavorant entrapped therein. This release, depending on factors such as the concentration of the active ingredient, may produce a "burst" of intense flavor, or perhaps a subtle blend of compatible and/or diverse flavors and essences.

Additionally, it is well known that various oat materials have intrinsic antioxidative properties. It has been shown that an emulsion using oat proteinaceous material (ca. 15% protein) as the emulsifier and mineral oil as the lipophilic phase can retard the onset of browning of sliced apples at least sixty hours when applied as a thin film to the cut surface of the apple, compared to approximately thirty minutes for untreated apple slices.

Moreover, it is also well known that various oat materials have intrinsic antipruritic properties. Thus, it would be apparent to one skilled in the art that an emulsion comprising oats as the proteinaceous material, when applied topically to the skin, is likely to exhibit such anti-itch properties.

The quantity of the active ingredient will vary depending upon the desired dosage or amount of active ingredient to be delivered in terms of either total volume or total elapsed delivery time, the viscosity and/or volatility of the active ingredient, and other parameters that will be apparent to one of skill in the art.

Proteinaceous Emulsifier

Useful proteinaceous emulsifiers include proteins derived from such varied and diverse sources as vegetables, grains, mammalian lactations, blood serum and avian ova. From the perspective of traditional protein classification, useful proteins include simple, conjugated and derived proteins. Suitable simple proteins include: albumins, globulins and glutelins. Suitable conjugated proteins include: nucleoproteins; glycoproteins and mucoproteins (also known collectively as glucoproteins); phosphoproteins (sometimes themselves classed as simple proteins); chromoproteins; lecithoproteins; and lipoproteins. Heat-coagulable derived proteins are also suitable.

Conjugated proteins are useful. Similarly, derived proteins (i.e., the products of various proteoclastic or denaturing processes) are also useful provided, of course, that they are not incompatible with the manifestation of the desired properties in the final product of the present process.

Derived proteins (i.e., the products of various proteoclastic or denaturing processes) are also useful as raw materials; provided, of course, that they are not, by virtue of their derivation, rendered incompatible with the manifestation of the desired properties of the emulsion of the present invention.

The preferred protein for a use in the present invention may vary according to considerations of availability and expense associated with the protein, as well as the nature of impurities in and other components of the protein source. Preferred proteins include those derived from vegetable or grain sources, particularly from grains or legumes including wheat, canola, beans, oats, peas, rapeseed, and soya, with particularly preferred proteins including oats, peas and beans. Sources of proteins which may be subject to treatment often contain various impurities which may negatively affect emulsion formation. It is desirable, therefore, that where proteins useful with the invention are naturally associated with insoluble components, these components be removable prior to processing.

A number of known processes exist for the preparation of a suitable proteinaceous material for use in the present invention. For example, in U.S. Pat. No. 4,089,848 to Bell, the isolation of a proteinaceous fraction from oats is disclosed by extracting lipids from the comminuted oats with a lipophilic solvent, carrying out alkaline and acid precipitation on the residue, and finally isolating the acid soluble protein. Oughton, in U.S. Pat. No. 4,154,728, describes another process for separating fractions of differing compositions from comminuted proteinaceous material from a variety of food sources including wheat, rye, barley, triticale, peas and buckwheat. The Oughton process comprises mixing the proteinaceous material with an aliphatic hydrocarbon or alcohol suitable to dissolve the lipids in the material. The wet slurry is distributed by means of centrifugation into fractions which differ primarily in protein composition. A similar process is applied to comminuted oats in U.S. Pat. Nos. 4,211,695 and 4,211,801 to Oughton.

To facilitate recovery of the protein in particulate form from the slurry produced in accordance with the foregoing processes, U.S. Pat. Nos. 4,208,259 and 4,208,260 to Oughton disclose the application of an electric field to the mixture and collection of a comminuted oat fraction which clings to the anode. An improved method of recovery is disclosed in U.S. Pat. No. 4,407,841 to Boocock, comprising the addition of aqueous ethanol to the slurry to agglomerate the proteinaceous material and facilitate separation thereof.

The protein particles are separated to a desired particle size or range of sizes, depending upon the desired properties of the emulsion film.

When the protein particulate is derived from natural grains and legumes, the particles will be irregular in shape, due to crushing and fragmenting during the milling process. However, median particle size can be determined by milling parameters or by using a series of graduated sieves or particle size analysis. Additionally, because of their natural origin, the protein particles of the present invention are fully biodegradable, there are no harmful polymer degradation products that could be released.

Many suitable protein concentrates or protein particulates are commercially available. For example, soya protein concentrate is available in 92% pure form from Protein Technologies International, St. Louis, Mo., USA. Pea protein concentrates are available from Woodstone Foods, Winnipeg, Canada.

The protein particulate is advantageously dried prior to use to remove water and other indigenous volatiles. In addition, depending upon the protein separation process, residual solvent could reside in the interstices of the particulate which could react adversely with the active ingredients of the emulsion.

Drying can be accomplished by any of a number of known methods, such as oven drying at elevated temperatures or subjecting the powder to a vacuum with or without the addition of heat. Alternatively, solvent extraction methods can be used, depending upon the particular requirements of the active ingredient and the end use of the emulsion.

Film Forming Emulsions

A particularly novel and unexpected aspect of the invention is that whereas the proteinaceous materials in the preferred embodiment are initially small particles, the emulsification process converts them to a much smaller colloidally dispersed form so that resultant films of the dried emulsion are translucent and smooth, with little or no visible evidence of particulate inclusions. The resultant network of proteinaceous particles is apparently in such intimate admixture with the oil constituents that there is virtually no surficial evidence of oiliness, even though relatively large amounts of oil may be entrapped within the film. In contrast to conventional formulations, substantial amounts of these films may be present on the skin without being visible or noticeable to the wearer, nor do the films rub off readily. Also, because of their colloidal nature (as opposed to solution behavior of conventional film-forming polymers), high concentrations of the proteinaceous emulsifiers can be employed without undue increase in emulsion viscosity.

By "film-forming," it is meant the ability of the emulsion to form a continuous solid film by air-drying of a deposited coating. In general, film-formability is enhanced by a number of factors, such as the size of the protein particulate emulsifier, which, in a preferred embodiment, may range from about 0.1 to about 700 microns, and preferably from about 1 to about 600 microns.

Specifically, it has been found that emulsions of relatively large proteinaceous particles may impart to an applied film a non-silky, gritty feel. For cosmetic applications, it has been found that emulsions using proteinaceous particles ranging in size from about 1 micron to about 10 microns in diameter are preferable for use in the emulsions of the present invention, in that they provide a silky, organoleptic quality to the thin film produced by the emulsion. In instances where it is desirable to have a relatively higher lipophilic phase content in the thin film, proteinaceous particles ranging in size from about 100 microns to about 600 microns have been found to be preferable for use in the emulsions of the present invention in that they allow for greater amounts of the lipophilic phase to be included in the emulsion, in comparison to smaller particles.

Materials with particles which can all pass through a Tyler #400 sieve (38 micron openings) may be preferable for use in the present invention for providing emulsion smoothness and avoidance of particulate inclusions in the dried film. Materials which fall into this category include peas, beans, and oats. The branny fraction of oats is typically highly oil sorptive and consists of particles having diameters approximating the 100–600 micron range.

Controlled Release

The present invention, when applied to a surface, is particularly efficacious in providing the release of the aforementioned active ingredients onto the surface. Those skilled in the art will appreciate that factors including: thickness of the film; composition of the emulsion, including the type of proteinaceous material; type of active ingredient; and concentration of the active ingredient, contribute in determining the type and rate of release of the active ingredient. Additionally, the release of the active ingredient may occur in a variety of ways, including: a single bolus release; a series of bolus releases; a continuous consistent release; and a continuous inconsistent release, all relating to the desired composition of the emulsion of the present invention.

The ability of the present invention to provide a controlled release of an active ingredient onto a surface is particularly useful in a variety of applications, including the controlled release of pharmaceuticals or pesticides. Once a particular active ingredient and compatible proteinaceous material are chosen, only routine experimentation is required to determine the proper emulsion composition and mode of application which will provide the desired rate and type of active ingredient release.

The emulsion of the present invention may release an active ingredient not only while in a dry form, but also during the drying of the emulsion onto a surface. For instance, when a typical emulsion of the present invention is spread thinly on skin or glass, it dries within a relatively few seconds, producing an occlusive film. The thickness of such a film is generally no greater than about a few mils. However, when a thicker coating is applied (on the order of ca. 0.5–3 mm), it requires approximately 100 times longer to dry out. Increased drying time arising from increased diffusion path length is expected due to the principles of diffusion.

Figure 2:
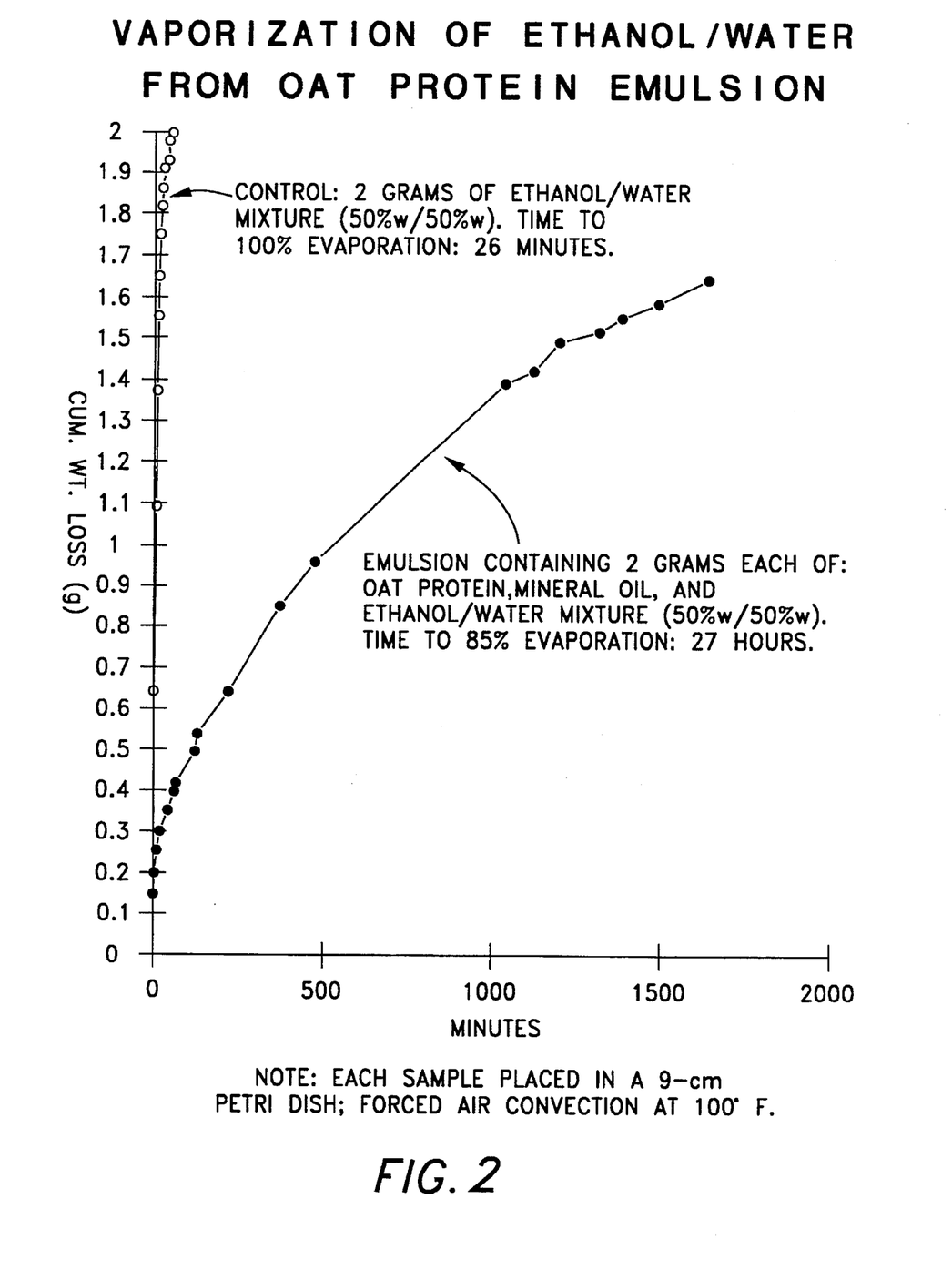
FIG. 2 is a graphic representation of the rate of vaporization of an ethanol/water mixture from an emulsion comprising oat protein as the proteinaceous emulsifier.
Figure 3:
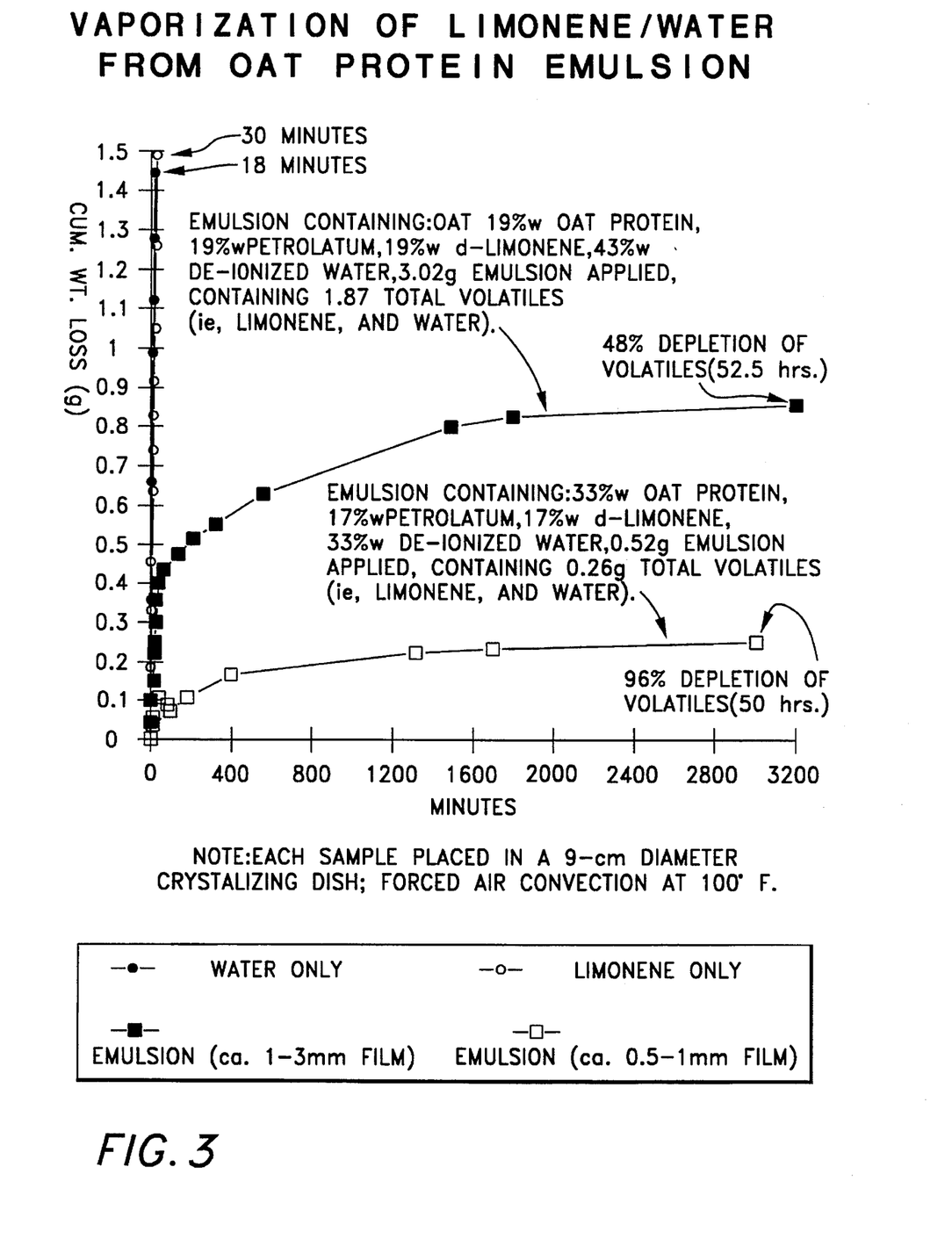
FIG. 3 is a graphic representation of the rate of vaporization of a limonens/water mixture from an emulsion comprising oat protein as the proteinaceous emulsifier.

Referring to the Figures, FIG. 2 shows 85% depletion of ethanol and water in 27 hours from an emulsion coating (estimated at 2–3 mm thick), whereas the control sample of ethanol/water evaporates in 26 minutes. (The oat material used in the emulsion contains ca. 15%w protein, d.b.). The ethanol and water were added to the emulsion simultaneously as aqueous phase constituents; hence, there is no volatiles loss being measured from the lipophilic .phase (which consists of mineral oil and the oat material).

FIG. 3 is similar to FIG. 2, except that limonene is in the lipophilic phase (along with oat material and petrolatum) and water is the sole constituent of the aqueous phase. A 1–3 mm coating of an emulsion (utilizing a 26%w protein branny fraction, particle size range predominantly 100–600μ) is only half depleted after more than two days of exposure (cf. rapid vaporization times of limonene and water controls).

A different emulsion applied at a thickness of ca. 0.5–1 mm volatilizes more quickly but, nonetheless, shows a significant residual compared to the controls. (The oat material in this emulsion is ca. 15%w protein with particle size range predominantly 1–10μ). Consonant with degree of depletion, the film had largely set up for this emulsion by the time the observation at 1682 minutes was made, whereas the ethanol/water emulsion coating was still soft and moist after 3150 minutes.

The above data are to be differentiated from the situation where a material is lost from a dried film which also provides the desired active ingredient release properties. Data relating to active ingredient release from dried films are as follows:

Pyrethrins:

a) A pyrethrins emulsion was prepared containing: 1 gram oat proteinaceous material (ca. 15% protein); 0.5 gram MGK 5192 (a pyrethrins concentrate also containing two synergists); and 0.5 gram mineral oil. These components were combined and then emulsified with 1.5 grams de-ionized water. This formulation was spread on the surface of a shallow glass dish, allowed to dry to a film, and placed in full sunlight for 8.5 hours. As a control, 0.5 grams MGK 5192 was placed in the same type of dish and given the same exposure to sunlight.

Both the pyrethrins and the synergists are photolabile and would be expected to decompose in sunlight. As shown in the table below, almost 2.5 times more pyrethrins remained in the dried emulsion film than in the control (as determined by gas chromatography). Similarly, there were 20% and 85% more synergists remaining in the film than in the control.

|  | Pyrethrins Remaining (%) | MGK 264 Remaining (%) | Piperonyl Butoxide Remaining (%) |
|---|---|---|---|
| Control | 9.5 | 77.7 | 41.1 |
| Film | 23.2 | 93.6 | 76.7 |

Fragrance:

b) A fragrance emulsion was prepared containing: 5 grams oat proteinaceous material (ca. 15% protein); 2.5 grams petrolatum; and 2.5 grams sandalwood fragrance (IFF 2883-AQ). These components were combined and then emulsified with 7.5 grams de-ionized water. This resulted in a beige-colored lotion which spread smoothly on the skin and produced a translucent film when dried on glass.

In a panel test, one drop of neat fragrance was applied to the back of the right hand and seven drops of the formulation were applied to the back of the left hand (corresponding to approximately equal amounts of fragrance on each hand). The right hand remained oily and glossy. The formulation dried quickly on the left hand to an invisible, non-greasy film. The fragrance on the left hand had a more rounded, mellower aroma compared to the harsher aroma of the neat fragrance on the right hand. Within five hours of application, the right hand had minimal detectable fragrance, whereas the left hand still exhibited a pleasant, consistent fragrance.

Other possible uses for the emulsion of the present invention include the use of the methodology in conjunction with the clean-up and/or control of spills or release of unwanted or dangerous agents into the environment, including the clean-up and control of oil spills. For instance, an appropriate proteinaceous material may be introduced to an area of oil release upon a body of water. Natural or artificial movement of the material into and throughout the oil and water sorbs the oil, thereby forming an emulsifiable concentrate which can then serve to emulsify the oil and produce a fine emulsion, more easily assimilated into the environment.

These emulsions can be dispersed into a large excess of water, in which case a colloidal suspension is formed wherein the water becomes turbid and the emulsion particles remain suspended for long periods of time. This method of providing a colloidal dispersion of oil may be particularily efficacious, in that microbial biodegradation of the oil can more easily occur. It has been observed that a form of the proteinaceous material which has buoyant properties may be particularly efficacious in such applications.

For example, 500 ml of Pacific Ocean seawater was placed in a beaker with a magnetic stir bar. A 1 gram piece of foamed protein particulate derived from oat grain (freeze dried) was added to the beaker after a few ml of 10W–30 motor oil had been dropped on the surface of the water. The protein particulate immediately upon addition to the water sorbed the majority of the oil. Agitation was initiated and continued for ca. 5 minutes. The protein particulate began to break up, with many exposed surfaces appearing white as a result of emulsification. In addition, there were observed many small white particles of the protein particulate admixed throughout the seawater when agitated, giving a flocculated appearance.

After another ca. 5 minutes of additional agitation, the seawater appeared quite turbid as a result of continued emulsification. After an additional ca. 5 minutes of agitation, the effects of the addition of the protein particulate were more pronounced: the water showed increased turbidity; there was an increase of flocculated protein particulate; and very little of the original motor oil appeared to be free in the seawater.

In an alternative embodiment, the active ingredient may be initially entrapped within the proteinaceous material when in the form of a particulate prior to the emulsion formation by a variety of methods which can be envisioned by one of ordinary skill in the art. For example, the active ingredient may be sprayed into the particulate in a liquid mist form while the particulate is maintained in constant motion. The necessary motion can be achieved in any of a variety of commercially available tumble dryers or other equipment designed for agitating such particulates. In addition, spouted bed dryers, fluidized bed dryers or other equipment which will be appreciated by one in the art can be used. Alternatively, the active ingredient can be dissolved in a suitable solvent and the protein particles immersed in the resulting solution with or without agitation. The introduction of many active ingredients into the structure of the protein particulate may be facilitated by performing the introduction step at elevated temperatures.

It is further anticipated that some nonactive ingredients such as surfactants (e.g., polysorbates) and cosolvents (e.g., alcohols) may be entrapped within the structure of the protein particulate to modify the release rates of the active ingredient.

If a solvent was used to carry an active ingredient into the protein particle, that solvent can be evaporated by heating or exposing to a vacuum, or both, depending upon the thermal stability of the active ingredient.

In a variation of the protein particulate of the present invention, an outer layer is provided to encapsulate the impregnated protein particle with an impermeable membrane, which may comprise either a solid or a liquid. In this embodiment, the release of the active ingredient will not commence until the membrane has been ruptured or dissolved. After the rupture or compromise of the outer membrane, the active ingredient will diffuse out of the protein particulate. For example, a water soluble membrane may be formed by coating the particle with an aqueous solution of polyvinyl alcohol, and then drying to form a film. Thus, liberation of the active ingredient occurs during the formation of the emulsion.

Another encapsulation technique is disclosed in U.S. Pat. No. 3,786,123 to Katzen. Katzen discloses the encapsulation of an active ingredient in gelatinized corn flour. According to that method, the active ingredient was thoroughly admixed with the corn flour and the resulting admixture was extruded in an extruder manufactured by the Wenger Mixer Manufacturing Company of Sabetha, Kans. The extruder was operated at a pressure of 1,000 psi and a temperature of 240° F. This temperature was selected as sufficient to gelatinize the corn flour yet not deleteriously affect a selected active ingredient. The gelatinized corn flour completely enclosed individual or groups of particles of the active ingredient.

By utilizing this or another known encapsulation method, attributes of both the sorptive matrix and the microencapsulation systems can be combined in conjunction with the film-forming emulsion of the present invention. This is particularly useful, as described, when a certain shelf life or other prolonged period will be necessary before the active ingredient contained within the protein particulate will be put to use with the film-forming emulsion.

Modification of Proteins:

Several methods are available to modify the protein particulate. These methods have been generally developed by protein chemists for peptide synthesis. These reactions are generally limited to carboxyl and amino groups in the alpha position. One such well-known method is that of Sheehan and Hess, J. Am. Chemical Soc. 77:1067 (1955). According to this method, the carboxyl group of the protein is activated by a water soluble carbodiamide such as 1-ethyl-3-(3-dimethylaminopropyl) carbodiamide. The carbodiamide-activated intermediate is reactive. The activated group can be further reacted with methionine and tryptophan. Processes for using these modifications of soya protein are known and are described by Voutsinas and Nakai, J.Food Sci. 44:1205 (1979).

The carbodiamide method and other protein derivatization methods can be used to attach molecules that affect the release rates of the active ingredient when in association with the protein particulate. Of course, the particular molecule attached will depend on characteristics of the active ingredient and the desired release profile. For example, lipid-type materials may be attached to slow the release of lipophilic active ingredients. Hydrogen bonding characteristics may also be used to slow release of appropriate active ingredients attaching molecules to which the active ingredient will hydrogen bond. Ligand or chelating derivatizing molecules capable of releasably binding the active ingredient are similarly contemplated.

Protein particulates modified by these methods can be used not only to tailor the rate of release, but also to achieve the necessary aesthetics for cosmetic and dermatological applications.

For the purpose of illustration, and not in any way to limit the applicable scope of the present invention, reference is made to the following examples:

EXAMPLE 1

Stages of Emulsification upon Progressive Addition of Water

Five grams of an oat protein concentrate were mixed with 5 grams of mineral oil. The oat protein concentrate contained 48% protein (dry basis) and consisted of fine, silky particles generally in the 1–10 micron size range. The resultant mixture (emulsifiable concentrate) was an oily, beige-colored opaque syrup. One gram of the emulsifiable concentrate was placed into each of six glass tubes. Various amounts of water were added at room temperature and stirred by hand.

(1) Control: emulsifiable concentrate alone. When applied to skin, the material remained quite greasy and did not rub in. On glass, the material appeared whitish and opaque, and remained very greasy.

(2) 10 pph de-ionized water (100 mg) added to the emulsifiable concentrate. Upon mixing, emulsification began and there was a slight lightening of color. Upon standing, there was a viscosity increase. The formulation remained very greasy when applied to both skin and glass. This formulation had the characteristics of a water-in-oil emulsion.

(3) 33 pph de-ionized water (330 mg) added to the emulsifiable concentrate. The mixture became a solid, gelatinous mass and was lighter in color than in (2). On skin, the formulation was greasy and hard to rub in initially; it eventually dried with a trace of greasiness. On glass, the formulation was difficult to apply and resulted in a greasy smear; the formulation was more translucent than (1) or (2). The material dried out on glass to leave an oily film. This formulation had the characteristics of an emulsion at, or near, the point of inverting to an oil-in-water emulsion.

(4) 50 pph de-ionized water (i.e., 500 mg) added to the emulsifiable concentrate. The mixture emulsified, producing a dramatic lightening of color and increase in viscosity. The resultant material was smooth and creamy. When applied to skin, the material was initially thick and sticky, but it disappeared and dried rapidly into an essentially invisible, non-greasy, unnoticeable film. The emulsion spread fairly evenly on glass to form a whitish film; the dried film was translucent, slightly oily when rubbed, and was substantive to glass. This formulation had the characteristics of an oil-in-water emulsion.

(5) 77 pph de-ionized water (i.e., 770 mg) added to the emulsifiable concentrate. The resultant material was lighter in color and thinner than in (4). The formulation was creamy but sticky when applied to skin. The material disappeared rapidly and dried to an essentially invisible, non-greasy, unnoticeable film. The material was difficult to spread evenly on glass and initially formed an opaque white film. Upon drying, the resultant film was translucent, slightly oily when rubbed, and substantive to glass.

(6) 100 pph de-ionized water (i.e., 1000 mg) added to the emulsifiable concentrate. The resulting lotion was somewhat thin and very light in color (off-white). The lotion was less viscous on the skin than in (5), but spread nicely and disappeared quickly. Similar to (4) and (5), it dried to an essentially invisible, non-greasy, unnoticeable film. When dried on glass, the film was thinner and more uniform than in (5) and more substantive to the glass surface. A representative photomicrograph of a dried mineral oil emulsion is shown at FIG. 5 (1000X; Zeiss Novascan 30 using Polaroid Type 55 film).

EXAMPLE 2

Emulsification with Various Proteinaceous Materials

The following formulations were mixed by hand at room temperature:

1) Defatted oat flour:

Five grams of defatted oat flour were combined with 5 grams mineral oil to yield a beige-colored paste with a somewhat grainy appearance. The oat flour contained 22.5% protein (dry basis) and consisted of a bi-modal distribution of particle sizes (generally, between 1–10 microns and 100–500 microns). A preservative was added in the amount of 0.2 grams (Germaben II, ex Sutton Laboratories).

Approximately 150 pph de-ionized water (15 grams) was added to the above mixture incrementally. The mixture emulsified to yield an off-white thin lotion, which applied to skin smoothly. However, because of the presence of larger particles (100–500 microns), the lotion appeared grainy on glass. The lotion dried as a non-greasy coating on both skin and glass. The formulation was stored overnight at 100° F. in a sealed vial. There was no separation of liquid or creaming. There was a slight, pleasant aroma.

2) Faba bean protein concentrate:

Five grams of faba bean protein concentrate (ca. 70% protein) were combined with 5 grams mineral oil and 0.2 grams Germaben II to yield a pale yellow-brown paste with a plastic-like consistency.

Approximately 100 pph de-ionized water (10 grams) were added to the above mixture incrementally. The mixture emulsified to yield a stringy, custard-colored lotion with a beany aroma. The lotion applied smoothly to skin. Initially, the lotion seemed oily; however, subsequently the oiliness disappeared. The resultant film was shiny and difficult to rub off. The formulation was stored overnight at 100° F. in a sealed vial. Minimal separation occurred during storage and the aroma was unimpaired. An identical formulation was prepared, except that the pre. servative was omitted. After being stored overnight at 100° F. in a sealed vial, the emulsion had degenerated into a cheesy material with a strong rancid odor, presumably the result of contamination.

3) Great northern white bean protein concentrate:

Five grams of great northern white bean protein concentrate (ca. 51% protein) was combined with 5 grams mineral oil to yield a smooth, pale yellow-brown syrup.

Approximately 100 pph de-ionized water (10 grams) was added to the above mixture incrementally. The mixture emulsified to yield an off-white, smooth lotion with a pungent beany aroma. This lotion applied nicely to both skin and glass and dried rapidly to a non-greasy, slightly glossy film. Germaben II (0.2 grams) was added and the formulation was stored overnight at 100° F. in a sealed vial. There was no separation and the aroma was unchanged after storage.

4) Soy flour:

Five grams of soy flour (54.8% protein, dry basis) were combined with 5 grams mineral oil to yield a mustard-colored viscous syrup.

150 pph de-ionized water (15 grams) was added to the above mixture incrementally. At both 50 and 75 pph water addition, a solid paste was formed with little evidence of emulsification. However, at 100 pph water addition, emulsification began and a very viscous yellow cream was produced. At 150 pph water addition, a smooth, thick lotion resulted. This lotion applied to skin smoothly and dried out rapidly to form a non-greasy film. However, the film attached tightly to the skin and was noticeable to the wearer; it also flaked off the skin fairly readily. On glass, the lotion appeared grainy.

5) Wheat flour:

Five grams of Wondra flour (Gold Medal brand, General Mills, also containing malted barley flour, 14.1% protein dry basis) were combined with 5 grams mineral oil to yield a gritty-looking thick white syrup.

Approximately 100 pph de-ionized water (10 grams) was added to the above mixture incrementally. The mixture emulsified to yield a creamy lotion. When applied to skin, the lotion dried quickly to form an invisible film. Particulate matter was observed within the film when the emulsion was applied to glass.

6) Amaranth flour:

Two grams of amaranth flour (14.8% protein, dry basis) were combined with 2 grams mineral oil to yield a very grainy, thick syrup containing brown particulates and white particulates.

75 pph de-ionized water (3 grams) was added to the above mixture incrementally. The mixture emulsified and became lighter colored and much thicker. The formulation applied to skin and glass fairly well and dried quickly as a non-greasy film. However, the material dried with a very grainy texture and flaked off both skin and glass readily. Germaben II was added (0.1 gram) and the mixture was stored overnight at 100° F. in a sealed vial. The formulation remained stable.

7) Buttermilk solids:

Two grams of buttermilk solids (ca. 23.6% protein) were combined with 2 grams mineral oil to yield a smooth, pale yellow opaque syrup.

75 pph de-ionized water (3 grams) was added to the above mixture incrementally. The mixture emulsified and became lighter colored and thicker; however, the emulsion was not as homogenous as for other materials. The emulsion did not dry as quickly and formed a film with a more oily feel relative to other emulsions. Germaben II was added (0.1 gram) and the mixture was stored overnight at 100° F. in a sealed vial. The formulation remained stable.

8) Barley flour:

Two grams of barley four (11.9% protein, dry basis) were combined with 2 grams mineral oil to yield a very grainy and thick paste. The paste was opaque and had a speckled yellow-brown color.

100 pph de-ionized water (4 grams) was added to the above mixture incrementally. The material emulsified and produced lotion with a grainy texture. This lotion did not apply smoothly to skin or glass, but dried quickly to a non-greasy film. Germaben II was added (0.1 gram) and the mixture was stored overnight at 100° F. in a sealed vial. The formulation remained stable.

9) Oat flour (full fat):

Two grams of full fat oat flour (16.7% protein, dry basis) were combined with 2 grams mineral oil to yield a very speckled honey brown thick syrup.

100 pph de-ionized water (4 grams) was added to the above mixture incrementally. A stringy, emulsified lotion resulted. The lotion was a beige color, containing brown flecks. It had a grainy texture when applied to skin, but dried with a non-greasy feel. On glass, the lotion dried as a grainy, non-oily translucent film. Germaben II was added (0.1 gram) and the mixture was stored overnight at 100° F. in a sealed vial. The formulation remained stable.

10) Unbleached white pastry flour:

Two grams of unbleached white pastry flour (11.2% protein, dry basis) were combined with 2 grams mineral oil to yield a pale yellow opaque syrup.

75 pph de-ionized water (3 grams) was added to the above mixture incrementally. The mixture emulsified and produced an off-white lotion. The lotion dried quickly on skin to form a non-greasy film. The dried emulsion produced a grainy film on glass. Germaben II was added (0.1 gram) and the mixture was stored overnight at 100° F. in a sealed vial. The formulation remained stable.

11) White rice flour:

Five grams of white rice flour (8% protein, dry basis) were combined with 5 grams mineral oil to yield a grainy, translucent syrup. Germaben II was added (0.2 gram).

Approximately 50 pph de-ionized water (5 grams) were added and the mixture emulsified. The mixture became thicker and whiter, but had a grainy texture. The emulsion applied and dried on skin and glass with an oily feel. One gram of white rice flour was added for additional emulsification. The emulsion thickened considerably. An additional 2.5 grams de-ionized water was added. The resultant coarse-looking white lotion was very grainy and contained some small, visible oil droplets. It dried to a greasy texture on both skin and glass.

12) Pea protein:

An emulsifiable concentrate was prepared containing 1 gram pea proteinaceous material (Propulse 985B ex Woodstone Foods, Winnipeg, Canada) and 1 gram mineral oil. 2.5 grams of de-ionized water were slowly added to the concentrate at room temperature. The mixture emulsified to yield a smooth, creamy lotion having a pale orange color. It applied smoothly to both skin and glass. It dried rapidly on skin to form an invisible, non-greasy film. It dried rapidly on glass to form a translucent, non-greasy film.

EXAMPLE 3

Effect of Protein Concentration on Emulsion Viscosity

Utilizing three different oat proteinaceous materials as emulsifiers, emulsions were prepared according to the following formula. The particle size for each emulsifier was predominantly in the 1–10 micron range.

| Ingredient | % by weight |
| --- | --- |
| Proteinaceous powder | 24.8 |
| Mineral oil | 24.8 |
| Germaben II | 1.0 |
| De-ionized water | 49.4 |
| | 100.0 |

The first three ingredients were combined to form an emulsifiable concentrate. Water was then added gradually to form the emulsion, using manual agitation at room temperature. Off-white, smooth lotions were formed in each case.

The viscosity was measured for each emulsion using a Cannon-Fenske viscometer, size 400, suspended in air at 24.5° C. A 10 ml sample of each emulsion was tested and the average flow time, based on three replicates, was recorded:

Emulsion 1: 56.7% protein, dry basis; average flow time, 239.1 seconds.

Emulsion 2: 11.2% protein, dry basis; average flow time, 120.3 seconds.

Emulsions 3: 34.0% protein, dry basis; average flow time, 143.3 seconds.

Figure 1:
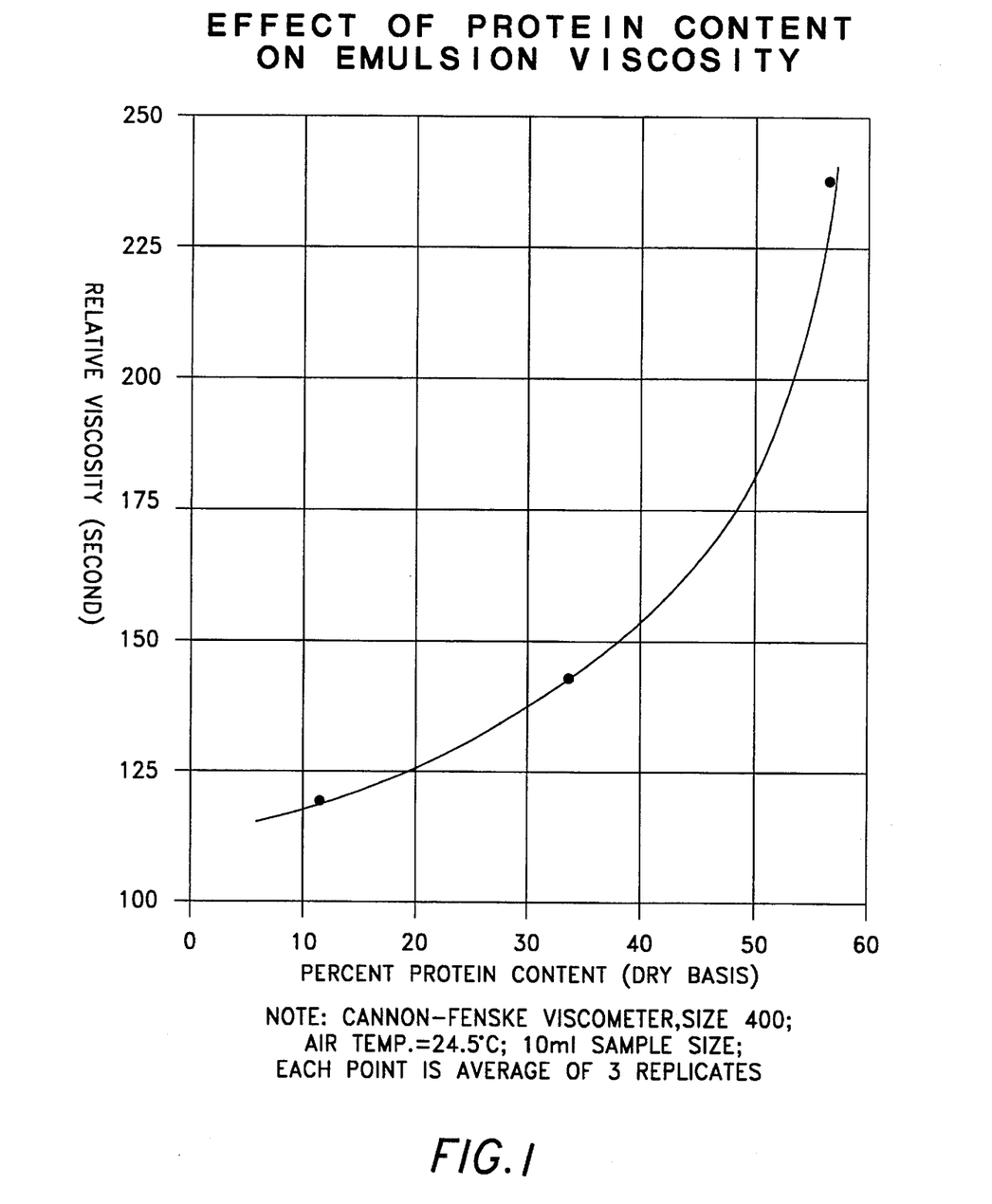
FIG. 1 is a graphic representation of the effect of the relative protein content of the proteinaceous emulsifier on the viscosity of the emulsion of the present invention.

As shown in FIG. 1 viscosity was found to increase exponentially with protein content of the emulsifier. The emulsions also differed in their application characteristics on skin and glass. However, all emulsions dried on skin and glass as a non-greasy film. All films on glass appeared translucent.

Skin application: Emulsion 1 (highest protein content) formed a noticeable, somewhat glossy film; also, this formulation tended to form thicker films than the other emulsions. The film from Emulsion 2 (lowest protein content) was completely unnoticeable. Emulsion 3 (intermediate protein level) formed a barely noticeable film.

Glass application: Emulsion 1 (highest protein content) seemed to form a thicker and more substantive film than the other emulsions. This film also seemed less oily when scraped. There was not much apparent difference in the films formed by Emulsions 2 and 3.

Each emulsion was placed in a closed vial and stored overnight at 100° F. All appeared the same after storage: trace of free liquid on surface, hint of creaming at top of emulsion, unchanged aroma.

EXAMPLE 4

Incorporation of Various Active Ingredients (Note: All materials were mixed with hand-stirring at room temperature.)

Lipophilic phase Addition of Active Ingredients

1) Vitamin E acetate: Five grams of an oat protein concentrate (48% protein, dry basis) were mixed with 5 grams of Vitamin E acetate (BASF) to yield a very thick tan syrup. A small amount of preservative was added to inhibit growth in the finished emulsion (0.2 grams Germaben II, Sutton Laboratories).

100 pph de-ionized water was gradually added and the system was observed to emulsify. The resulting lotion had an off-white color and appeared smooth. It dried rapidly to form a non-oily invisible film on the skin.

2) Octyl methoxycinnamate: Five grams of an oat protein concentrate (48% protein, dry basis) were mixed with 5 grams of octyl methoxycinnamate, a sunscreen agent, to yield a honey-brown syrup. Germaben II (0.2 grams) was added as a preservative.

This concentrate was emulsified by the gradual addition of ca. 75 pph de-ionized water (7.5 grams). The resultant off-white lotion dried upon application to the skin to form a non-oily invisible film.

It was noted that overly brisk rubbing of the lotion prior to dry-out on the skin tends to remove the protein emulsifier (which balls up under the applying fingers). However, it was found extremely difficult to remove the film by rubbing once it has dried. This phenomenon is typical for the emulsions of this invention.

3) N,N-diethyl-m-toluamide (DEET): Five grams of an oat protein concentrate (48% protein, dry basis) were mixed with 5 grams of DEET, an insect repellent agent, to yield a honey-brown translucent syrup. Germaben II (0.2 grams) was added as a preservative.

This concentrate was emulsified by the gradual addition of ca. 75 pph de-ionized water (7.5 grams). The resultant off-white lotion dried rapidly upon application to the skin to form a non-oily invisible film with a characteristic DEET aroma.

4) (R)(+) limonene: Five grams of an oat protein concentrate (48% protein, dry basis) were mixed with 2 grams of limonene, a volatile essential oil, to yield a thick beige syrup.

This concentrate was emulsified by the gradual addition of 150 pph de-ionized water (10.5 grams). The resultant off-white, thick, creamy lotion dried rapidly upon application to the skin to form a non-oily invisible film with a characteristic limonene aroma. Interestingly, as the limonene volatilized from the film, a white residue gradually formed on the skin. This occurs because the oat protein concentrate is the only remaining ingredient after initial volatilization of water (hence forming the film) and subsequent volatilization of limonene.

5) DEET/mineral oil combination: Five grams of an oat protein concentrate (48% protein, dry basis) were mixed with 3 grams of DEET and 2 grams mineral oil to yield a very thick honey-brown paste. Germaben II (0.2 grams) was added as a preservative.

This concentrate was emulsified by the gradual addition of ca. 100 pph de-ionized water (10 grams). The resultant off-white lotion dried rapidly upon application to skin and glass to form a non-oily film with a characteristic DEET aroma. The film was invisible on skin and translucent on glass.

DEET and mineral oil are immiscible, but co-emulsified nicely in this formulation. Overnight storage in a sealed vial at 100° F. showed good emulsion stability. The formulation was found to repel both mosquitos and black flies when applied in a thin film to a subject's skin.

6) Vaseline petroleum jelly: Five grams of a proteinaceous oat powder (ca. 15% protein) were mixed with 5 grams of Vaseline, an emollient, to yield a very thick beige paste.

This concentrate was emulsified by the gradual addition of ca. 75 pph de-ionized water (7.5 grams). The resultant thick, off-white lotion disappeared and dried virtually instantaneously upon application to the skin to form a non-oily invisible film.

7) Synergized pyrethrins: Six grams of a proteinaceous oat powder (ca. 15% protein) were mixed with 2.5 grams MGK 5192 (McLaughlin, Gormley and King, Minneapolis, Minn.), an insecticidal concentrate containing pyrethrins, synergists and petroleum distillate, to yield a thick, yellow-brown plastic syrup.

This concentrate was emulsified by the gradual addition of 120 pph de-ionized water (10 grams). The resultant creamy, pale beige lotion applied smoothly to glass and leaf surfaces. A whitish, translucent substantive film was formed on glass; a semi-gloss substantive film formed on leaves.

8) Pre-entrapped synergized pyrethrins: 0.56 gram MGK 5192 was dissolved in 3 grams hexanes and added to 4.44 grams of a proteinaceous oat powder (15.0% protein, dry basis). The hexanes were flashed off, resulting in 5 grams of a light tan, fine powder containing 1%w pyrethrins. Five grams of mineral oil and 0.2 gram Germaben II were added to this powder to yield a pale mustard-colored opaque syrup.

This concentrate was emulsified by the gradual addition of ca. 75 pph de-ionized water (7.5 grams). The resulting emulsion was sprayed with a trigger sprayer onto. foliage and dried rapidly without a noticeable residue. Upon application to glass, a non-oily substantive, translucent film was formed.

However, upon the initial addition of water, the formulation resisted emulsification. This suggests that the proteins were initially tied up by the pre-entrapped pyrethrins.

9) N,N-diethyl-m-toluamide (DEET) and octyl methoxycinnamate combination: Seven grams of a proteinaceous oat powder (15.0% protein, dry basis) were mixed with 2.5 grams of DEET and 2.5 grams of octylmethoxycinnamate sunscreen to yield a thick honey-brown syrup. Germaben II (0.2 grams) was added as a preservative.

This concentrate was emulsified by the gradual addition of ca. 75 pph de-ionized water (9 grams). The resultant smooth, creamy, pale beige lotion applied smoothly to skin and glass and dried rapidly to form a non-oily film. The film was invisible on skin and translucent on glass.

10) Natural and Synthetic Oils: Emulsions were prepared with a variety of oils using the following general recipe:

5.0 g oat proteinaceous material (15% protein)

5.0 g oil 0.2 g Germaben II 7.5 g de-ionized water

The first three ingredients were mixed together to form an emulsifiable concentrate, typically with a viscous character. Then, water was slowly added to form the emulsion at room temperature. The following oils were used: olive oil; corn oil; soybean oil; sesame oil and sgualane (Fitoderm ex Centerchem, N.Y.). In all cases, the emulsions were smooth and creamy and could be dried on a surface to form a non-greasy film. When stored overnight in sealed vials in a 38° C. oven, there was no separation or apparent degradation of the emulsions.

It would be apparent to one of skill in the art that other types of oil could be readily emulsified in the above fashion, including various lanolin oils, petroleum oils and silicone oils.

Aqueous Phase Addition

1) Aloe vera gel: Five grams of an oat protein concentrate (48% protein, dry basis) were mixed with 5 grams of mineral oil to yield a thick beige syrup. Germaben II (0.2 gram) was added as a preservative.

This concentrate was emulsified by the gradual addition of ca. 100 pph aloe gel (Tri-K Industries), (10 grams). The resultant off-white lotion applied smoothly to skin and glass and dried rapidly to form a non-oily film. The film was invisible on skin and translucent on glass.

2) Liposomes: Two grams of a proteinaceous oat powder (ca. 15% protein) were mixed with 2 grams of mineral oil to yield a light tan syrup.

This concentrate was emulsified by the gradual addition of 50 pph of a 10% liposome aqueous dispersion (Princeton Lipids) (2 grams). The resultant thick, off-white cream disappeared virtually instantaneously on skin and dried rapidly, forming an invisible, non-greasy film. The cream formed a soft, translucent, non-oily film on glass.

3) *Bacillus thuringiensis* protoxin: Five grams of an oat protein concentrate (48% protein, dry basis) were mixed with 5 grams of mineral oil to yield a thick beige syrup. Three mg of *Bacillus thuringiensis* protoxin, an insecticide, was solubilized in caustic solution at 11.4, followed by neutralization with HCl to pH 6.3. The Bt solution (15.9 grams) was used to emulsify the syrup, yielding a beige emulsion. The emulsion dried to a translucent film on glass and exhibited good adhesion.

4) Salicylic acid: Five grams of a proteinaceous oat powder (15.0% protein, dry basis) were mixed with 5 grams of mineral oil to yield a thick beige syrup.

This concentrate was emulsified by the gradual addition of 75 pph de-ionized water (7.5 grams). Then, 1.5 grams of 20% w/w salicylic acid (in ethanol) was mixed in and the alcohol was flashed off. Germaben II (0.2 grams) was added as a preservative.

The resultant off-white lotion contained 1.7% w/w salicylic acid. It applied smoothly to skin and glass and dried rapidly to form a non-oily film. The film was invisible on skin and translucent on glass. There was no evidence of salicylic acid crystals. Salicylic acid is used as the active ingredient for various dermal medications, e.g., as an anti-acne agent.

5) Aluminum/zirconium tetrachlorohydrex: Five grams of a proteinaceous oat powder (ca. 15% protein) were mixed with 5 grams of mineral oil to yield a thick beige syrup.

This concentrate was emulsified by the gradual addition of a 50% aqueous solution of Rezal 36GP, an antiperspirant (Reheis Chemical). 125 pph of solution was added (12.5 grams) and formed a light tan lotion. When applied to skin, a thick, semi-gloss, non-oily film was formed.

Aqueous and Lipophilic Phase Addition of Active Ingredient

1) Vitamin E acetate (lipophilic phase)/aloe vera gel (aqueous phase): Five grams of a proteinaceous oat powder (15.0% protein, dry basis) were mixed with 5 grams of vitamin E acetate (BASF) to yield a very thick tan syrup. Germaben II (0.2 grams) was added as a preservative.

This concentrate was emulsified by the gradual addition of ca. 100 pph aloe gel (Tri-K Industries) (10 grams). The resultant off-white lotion applied smoothly to skin and glass and formed a non-greasy film. The film was invisible on skin and translucent on glass.

Food Extracts

An emulsion based on an oily extract of black pepper was prepared. The emulsifiable concentrate was prepared by blending 5 grams of extract with 5 grams of a proteinaceous oat material (ca. 15%w protein, d.b.). The result was a thick greenish syrup. Ten grams of de-ionized water was slowly added, and the mixture emulsified to yield a smooth, creamy lotion with a green color. The emulsion dried on glass to give a translucent film with a pronounced pepper aroma. Similar results were obtained when emulsions were prepared with strawberry flavor extract and capsaicin flavor extract. Each material was palatable and imparted a convincing flavor when mixed with an appropriate food (4 parts black pepper emulsion per 10,000 parts cream of potato soup; 4 parts capsaicin emulsion per 250,000 parts re-fried beans; 4 parts strawberry emulsion per 1,000 parts vanilla ice cream).

Entrapment of-an Emulsion:

An emulsifiable concentrate was prepared by mixing equal parts of an oat proteinaceous material (15% protein) and mineral oil. To 100 parts of the emulsifiable concentrate, 75 parts of de-ionized water were added. A smooth, beige-colored lotion was formed.

This emulsion was progressively added to five grams of a proteinaceous oat material (24% protein, dry basis; predominant particle size range, 100–600 microns). After 5 grams addition, the proteinaceous material was still a dry powder, having successfully entrapped the emulsion. This technique thereby would allow the entrapment of otherwise insoluble solids in proteinaceous microparticles (by first emulsifying them into colloidal form via the invention described herein).

An additional 10 grams of emulsion was added and the proteinaceous material began to become pasty. The mixture was placed on a rotary evaporator for about one hour (24 in. Hg., 133 RPM, 81° C.). A dry particulate material resulted, which readily emulsified upon the addition of water.

Although this invention has been described in terms of certain preferred embodiments and applications, other embodiments and applications that are apparent to those of ordinary skill in the art are also within the scope of this invention. Accordingly, the scope of the invention is intended to be defined only by reference to the appended claims.

I claim:

1. A method of forming a film on a surface, comprising:

providing an effective amount of a film-forming emulsion comprising an emulsifier consisting essentially of a proteinaceous particulate material derived from oat seed by a process that substantially alters the seed only by milling to a particle size range of about 0.1 microns to about 700 microns, physical separation of milled seed components to select a non-branny fraction that substantially passes through a 400 mesh screen, and organic solvent extraction, in combination with a lipophilic phase and an aqueous phase at room temperature, said proteinaceous particulate material functioning as the primary emulsifying agent;

applying said emulsion to a surface such that said emulsion forms a thin layer; and permitting the aqueous phase in said layer to evaporate, thereby forming a smooth, durable, dry film on said surface, wherein the formation of said film is attributable to said proteinaceous particulate material.

2. The method of claim 1, further comprising the step of providing an active ingredient in said emulsion.

3. The method of claim 2, wherein said lipophilic phase comprises said active ingredient.

4. The method of claim 2, wherein said aqueous phase comprises said active ingredient.

5. The method of claim 1, wherein said emulsion is a topical composition.

6. The method of claim 5, wherein said lipophilic phase comprises a pharmaceutical compound.

7. The method of claim 5, wherein said lipophilic phase comprises a moisturizer.

8. The method of claim 5, wherein said lipophilic phase comprises a sunscreen.

9. The method of claim 5, wherein said lipophilic phase comprises an insect repellent.

10. The method of claim 11, wherein said surface is skin.

11. The method of claim 10, wherein said emulsion is a cosmetic emulsion.

12. The method of claim 10, wherein said emulsion is a pharmaceutical emulsion.

* * * * *

UNITED STATES PATENT AND TRADEMARK OFFICE
CERTIFICATE OF CORRECTION

PATENT NO. : 5,589,195  
DATED : December 31, 1996  
INVENTOR(S) : Richard C. Potter Page 1 of 1

It is certified that error appears in the above-identified patent and that said Letters Patent is hereby corrected as shown below:

<u>Column 20,</u>
Line 35, cancel "11" and replace it with -- 1 -- .

Signed and Sealed this

Twenty-first Day of May, 2002

*Attest:*

*Attesting Officer*

JAMES E. ROGAN
*Director of the United States Patent and Trademark Office*